(12) United States Patent
Minges

(10) Patent No.: US 8,726,721 B2
(45) Date of Patent: May 20, 2014

(54) APPARATUS AND METHOD FOR MONITORING AND SAMPLING AIR QUALITY IN AN INTERIOR SPACE OF A WALL

(76) Inventor: Charles Mitchell Minges, Naples, FL (US)

( * ) Notice: Subject to any disclaimer, the term of this patent is extended or adjusted under 35 U.S.C. 154(b) by 484 days.

(21) Appl. No.: 13/197,025

(22) Filed: Aug. 3, 2011

(65) Prior Publication Data

US 2013/0035869 A1    Feb. 7, 2013

(51) Int. Cl.
*G01N 19/10* (2006.01)
(52) U.S. Cl.
USPC .............. 73/31.01; 73/864.34; 73/864.35; 73/864.53
(58) Field of Classification Search
USPC ............ 73/31.01, 864.35, 864.34, 864.53
See application file for complete search history.

(56) References Cited

U.S. PATENT DOCUMENTS

| | | |
|---|---|---|
| RE28,154 E | 9/1974 | Stiles |
| 3,903,745 A | 9/1975 | Bolser |
| 5,500,369 A | 3/1996 | Kiplinger |
| 5,553,006 A | 9/1996 | Benda |
| 5,611,846 A | 3/1997 | Overton et al. |
| 5,798,945 A | 8/1998 | Benda |
| 5,874,097 A | 2/1999 | Henderson et al. |
| 5,881,951 A | 3/1999 | Carpenter |
| 5,922,939 A | 7/1999 | Cota |
| 6,206,968 B1 | 3/2001 | Minges |
| 6,314,789 B1 * | 11/2001 | Peter .............................. 73/23.2 |
| 6,352,703 B1 | 3/2002 | Henderson et al. |
| 6,472,203 B1 | 10/2002 | Gallup et al. |
| 6,514,721 B2 | 2/2003 | Spurrell |
| 6,965,708 B2 | 11/2005 | Luo et al. |
| 7,382,269 B2 | 6/2008 | Remsburg |
| 7,522,036 B1 * | 4/2009 | Preuss et al. ................... 340/531 |
| 7,658,096 B2 | 2/2010 | Pinto et al. |
| 7,743,552 B2 | 6/2010 | Borth et al. |
| 8,138,430 B1 * | 3/2012 | Ucero ........................... 174/480 |
| 2003/0008341 A1 | 1/2003 | Spurrell |
| 2003/0115978 A1 | 6/2003 | Moehnke et al. |
| 2007/0026107 A1 | 2/2007 | Wang et al. |
| 2007/0181000 A1 * | 8/2007 | Wilson et al. .................... 96/134 |
| 2008/0148624 A1 | 6/2008 | Borth et al. |
| 2009/0064759 A1 | 3/2009 | Pettit et al. |
| 2009/0064803 A1 | 3/2009 | Pettit et al. |
| 2009/0135006 A1 * | 5/2009 | Schoettle ....................... 340/540 |
| 2009/0137163 A1 * | 5/2009 | Schoettle ....................... 439/894 |
| 2010/0078494 A1 | 4/2010 | Mularoni et al. |
| 2011/0080255 A1 | 4/2011 | Borth et al. |
| 2011/0109301 A1 * | 5/2011 | Johnson et al. ............... 324/119 |
| 2011/0182012 A1 * | 7/2011 | Hilton et al. ............. 361/679.01 |

* cited by examiner

*Primary Examiner* — Hezron E Williams
*Assistant Examiner* — Rodney T Frank
(74) *Attorney, Agent, or Firm* — The Law Office of James E. Ruland, PLC

(57) ABSTRACT

An apparatus and method for monitoring and sampling air quality in an interior space of a wall are provided. The apparatus includes a housing configured to attach the apparatus to an electrical outlet in the wall, and a gasket configured to provide a seal between the housing and the electrical outlet. The apparatus further includes an air moving unit configured to draw air from the interior space of the wall into the apparatus, and a sensor configured to monitor and sample the air quality in the interior space of the wall. The gasket is configured to directly attach to an electrical plate cover of the electrical outlet or to the wall.

21 Claims, 6 Drawing Sheets

APPARATUS AND METHOD FOR MONITORING AND SAMPLING AIR QUALITY IN AN INTERIOR SPACE OF A WALL

BACKGROUND

1. Field

Embodiments of the invention relate to an apparatus and method for monitoring and sampling air quality in an interior space of a wall. More specifically, certain embodiments of the invention are directed to a self-supporting and self-sealing apparatus for measuring psychrometric air qualities in an interior space of a wall through an electrical outlet in the wall. Some embodiments of the invention are further directed to monitoring and sampling the air quality in the interior space of the wall to identify the presence of mold spores or other airborne contaminants.

2. Description of the Related Art

Conventional methods for mold testing include air testing, surface testing, and bulk (material) testing. Surface testing and bulk testing are not practical for a preliminary investigation for mold when conditions are pre-symptomatic or not indicative of mold damage. Air testing, on the other hand, is useful for ascertaining spore concentrations in the air and contrasting the results with a similar sample obtained from the outdoors. If the indoor air is shown to contain a higher concentration of mold spores than the outdoor test, then it may be inferred that the home interior is generating mold growth.

Conventional methods for sampling air within an interior space in the wall include, for example, (1) drilling or punching holes in the wall and inserting an intake from a remote air sampling pump, (2) removing baseboards and inserting the intake from the remote air sampling pump, and (3) removing an electrical outlet or switch plate cover and inserting a tube with an intake through the electrical outlet which may require a hole to be bored or a knock out (standard to the boxes) to be moved. The insertion of the tube through the electrical junction box, however, has three drawbacks.

First, the insertion of an uptake (or probe) does not seal off the interior wall air from the interior room air, requiring the intake or tube be inserted through the electrical box, so that the intake or tube primarily draws air from an interior space well within the wall away from the electrical box which is now exposed to room air.

Second, this method requires the boring of a hole or punching the knock out common to electrical outlet boxes. Once a hole has been made in the electrical outlet box, the intake or tube must be inserted and later removed after use.

Third, the exposed electrical power outlet must be powered down. When metal drill bits, screwdrivers, metal punches, sensor probes, or intakes are used, the electricity must be turned off to the electrical outlet during the boring, the insertion, the testing, and the removal of the uptake or probe to avoid any electrical shock or shorting of the electrical power outlet.

Another conventional method is to remove the electrical power outlet or switch plate cover and bore a hole directly below or around the exterior of the electrical outlet box. This method avoids direct drilling, inserting, and removal of the uptake or probe through the electrical outlet box. However, because there is small area between the standard mounting flange of a 110 power receptacle and the outlet cover plate, which attaches the electrical outlet or switch to the electrical box, this method does not reliably assure that the electrical outlet cover plate will conceal the entire hole. Wiring and wall supports around the electrical outlet can also complicate the boring process. This method, therefore, may require the fitting of an oversized outlet cover to conceal the hole.

SUMMARY

In accordance with an embodiment of the invention, there is provided an apparatus for monitoring and sampling air quality in an interior space of a wall, which includes a housing configured to attach the apparatus to an electrical outlet in the wall, and a gasket configured to provide a seal between the housing and the electrical outlet. The apparatus further includes an air moving unit configured to draw air from the interior space of the wall into the apparatus, and a sensor configured to monitor and sample the air quality in the interior space of the wall. The gasket is configured to directly attach to an electrical plate cover of the electrical outlet or to the wall.

In accordance with another embodiment of the invention, there is provided an apparatus for monitoring and sampling air quality in an interior space of a wall, which includes a housing configured to attach the apparatus to an electrical outlet in the wall, a gasket configured to provide a seal between the housing and the electrical outlet, a plug including one or more prongs to secure the housing to the electrical outlet in the wall, and a nipple operatively connected to the vented chamber. The gasket is configured to directly attach to an electrical plate cover of the electrical outlet or to the wall. The nipple is configured to receive a pump to displace air through the apparatus into an interior space of the wall.

In accordance with another embodiment of the invention, there is provided another apparatus for monitoring and sampling air quality in an interior space of a wall, which includes attaching means for attaching the apparatus to an electrical outlet in the wall, and sealing means for providing a seal between the attaching means and the electrical outlet. The apparatus further includes air moving means for drawing air from the interior space of the wall into the attaching means, and sensing means for monitoring and sampling the air quality in the interior space of the wall. The sealing means is for directly attaching the apparatus to an electrical plate cover of the electrical outlet or to the wall.

In accordance with another embodiment of the invention, there is provided a method for monitoring and sampling air quality in an interior space of a wall, which includes attaching, using a housing, an apparatus to an electrical outlet in the wall, and providing a seal between the apparatus and the electrical outlet. The method further includes drawing air from the interior space of the wall into the apparatus, and monitoring and sampling, using a sensor, the air quality in the interior space of the wall. The attaching includes directly attaching the apparatus to an electrical plate cover of the electrical outlet or to the wall.

In accordance with another embodiment of the invention, there is provided a computer program product embodied on a non-transitory computer readable storage medium. The computer program product is encoded with instructions to control a processor to perform a process for monitoring and sampling air quality in an interior space of a wall. The process includes attaching, using a housing, the apparatus to an electrical outlet in the wall, and providing a seal between the apparatus and the electrical outlet. The process further includes drawing air from the interior space of the wall into the apparatus, and monitoring and sampling, using a sensor, the air quality in the interior space of the wall. The attaching includes directly attaching the apparatus to an electrical plate cover of the electrical outlet or to the wall.

BRIEF DESCRIPTION OF DRAWINGS

Further aspects, details, advantages and modifications of the invention will become apparent from the following detailed description of the embodiments, which is to be taken in conjunction with the accompanying drawings, in which.

DETAILED DESCRIPTION

It will be readily understood that the components of the invention, as generally described and illustrated in the figures herein, may be arranged and designed in a wide variety of different configurations. Thus, the following detailed description of the embodiments of the apparatus and the method for monitoring and sampling air quality in an interior space of a wall, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For examples, the use of the phrases "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," or other similar language, throughout this specification do not necessarily all refer to the same group of embodiments, and the described features, structures, or characteristics may be combined in any suitable manner in one or more embodiments.

If desired, the different functions discussed below may be performed in a different order and/or concurrently with each other. Furthermore, if desired, one or more of the above-described functions may be optional or may be combined. As such, the foregoing description should be considered as merely illustrative of the principles, teachings and embodiments of this invention, and not in limitation thereof.

Some embodiments of the invention combine hardware and software components to create an apparatus and method for air monitoring as practiced by indoor air quality (IAQ) inspectors, home inspectors, industrial hygienists, environmental consultants, related trades people, and for home use by a homeowner. The air monitoring includes, for example, air sampling and testing of an interior space of a wall through an electrical outlet in the wall.

Figure 1:
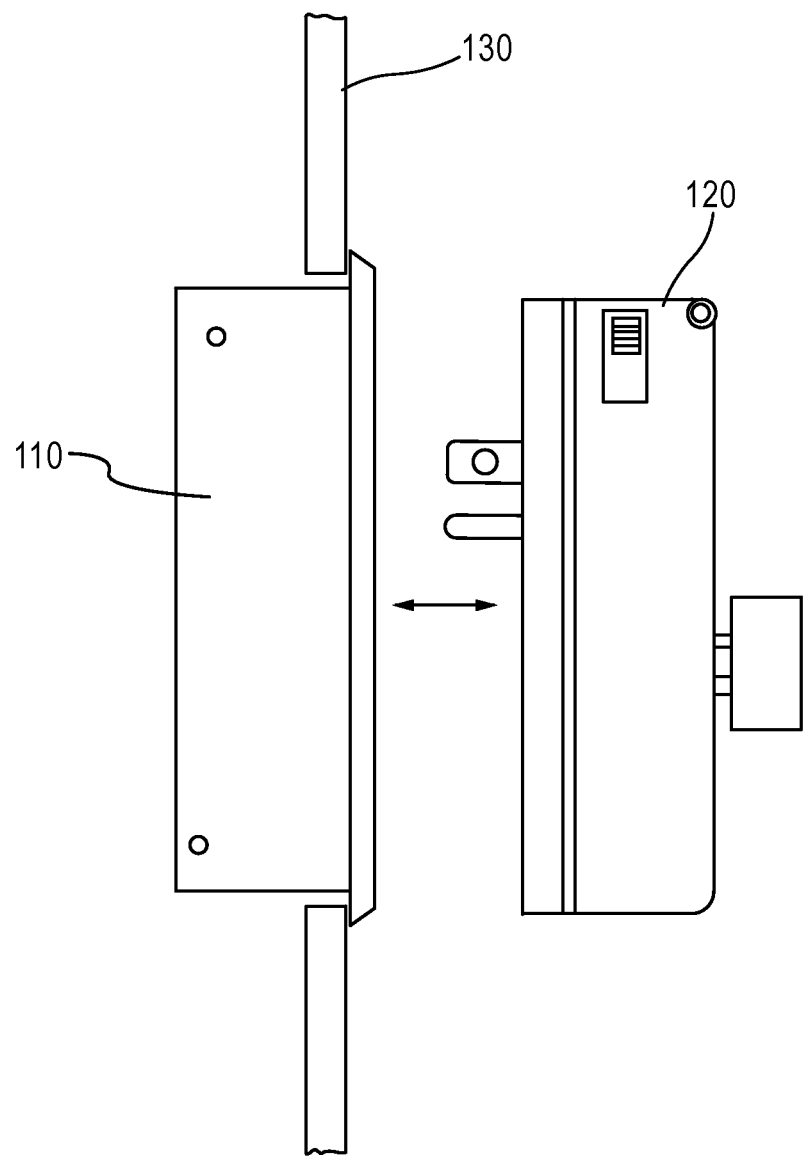
FIG. 1 shows a schematic diagram of a system for monitoring and sampling air quality in an interior space of a wall, in accordance with an embodiment of the invention.

FIG. 1 shows a schematic diagram of a system for monitoring and sampling air quality in an interior space of a wall, in accordance with an embodiment of the invention. In accordance with an embodiment of the invention, the system 100 includes an electrical unit 110 in a wall and a device 120 configured to monitor and sample air quality in an interior space 130 of the wall.

The electrical unit 110 may include, for example, an electrical outlet, a switch plate or outlet cover, an electrical receptacle, an electrical mounting box, and a cutout in a wall board. The interior space 130 of the wall may include one or more battens or studs and the wall board, which collectively define the interior space 130 of the wall. The interior space 130 of the wall is hollow and may include an insulation material. The electrical unit 110 is fitted into a cavity in the interior space 130 of the wall. According to some embodiments of the invention, the electrical outlet, the switch plate or outlet cover, the electrical receptacle, the electrical mounting box, and the cutout in the wall board are collectively used as a plenum to sample air from within the interior space 130.

In accordance with an embodiment of the invention, the device 120 includes housing which universally mounts the device 120 to the electrical unit, for example, a standard 110V electrical wall outlet or a 220V electrical wall outlet. The device 120 connects to various devices for drawing and sampling the air in the interior space 130 of the wall, and for introducing gas or air particulates into the interior space 130 of the wall to treat any contaminants, for example, mold spores, found therein.

The device 120 provides a convenient and efficient method for air sampling within the interior space 130 of the wall, for example, for measuring psychrometric air qualities (e.g., temperature, relative humidity, and dew point), which are not normally measured, within the interior space 130 of the wall. The device 120 permits air sampling without boring additional holes into the wall. Specifically, the device 120 allows common tools and methodology to be utilized while obviating the need for drilling or punching holes through interior wall elements, such as sheetrock, plaster, or other materials. The device 120 further eliminates the need and expense of subsequent repair and touch-up painting to the punctured wall which is common in conventional air sampling processes.

For exploratory purposes, the device 120, in accordance with an embodiment of the invention, measures air quality in the interior space 130 of the wall through the use of common and readily available electrical junction boxes which contain electrical outlets, i.e., through electrical unit 110. The device 120 converts common 110V or 220V outlets, and the electrical junction boxes to which they mount, into plenums through which air can be withdrawn. In operation, the device 120 is plugged into the electrical unit 110 and forms a seal around the electrical unit 110 and the wall. The device 120 extracts air through the electrical outlet box of the electrical unit 110 and directly through gaps present between the electrical outlet box and the wallboard material within which the electrical outlet box is set. These vented areas provide access to the interior space 130 of the wall so that air can be withdrawn by the device 120. The device 120 draws the air into a common chamber of the device 120 for monitoring the air quality in the interior space 130 of the wall. Based on this monitoring activity, the device 120 may measure and record, for example, temperature, relative humidity, and dew point of the air, high and low values for these psychrometric air qualities, and may further provide audible and visual alarms for preset conditions. For example, in accordance with one embodiment of the invention, the device 120 alerts a homeowner to damp and humid conditions which may be detrimental to both human health and home values.

As briefly mentioned above, the device 120 connects to various devices for drawing and sampling the air in the interior space 130 of the wall or for introducing gas or air particulates into the interior space 130 of the wall to treat any contaminants, for example, mold spores, found therein. In accordance with an embodiment of the invention, the device 120 includes an exhaust port which connects to various filters and collection media to sample the withdrawn air for mold spores and possibly other airborne contaminates. For example, the invention may be fitted with nutrient filled collection media, for example, agar-based cultures, filled cassettes and dishes, and media filled with malt extract dextrose (MEA), or similar nutrient-based solutions which encourage mold growth for detection purposes. Such non-quantitative testing is useful for detecting the presence of mold within the confined interior space 130. The device 120 may further be used in conjunction with quantitative testing involving laboratory analysis by being coupled to a calibrated pump, which allows the user to know the quantity of air being pumped through the device 120, the amount of time, the velocity and volume of the air being displaced. The sampled air may be captured and further analyzed in a professional laboratory. The device 120 may also measure regular air when an extraction pump in the device 120 is in an off mode.

In accordance with an embodiment of the invention, the device 120 facilitates the sampling and detection of mold growth within the interior space 130 of the wall. It should be noted that air within the interior space 130 of the wall is affected by both the interior and exterior air temperatures. A high deferential between the two temperatures subjects this space to increased moisture problems, including condensation and dew-point activity. Leaks, water, and air intrusion may also contribute to moisture buildup. This moist environment is conducive to mold grow which has a real and perceived threat both to human (and even pet) health and property values. Mold spores are naturally occurring and are introduced into the home from outdoor sources. The mold spores require a favorable temperature, moisture, and a food source to survive and grow. For example, the paper lining of conventional gypsum board (sheetrock) and the use of wood within the interior space 130 of the wall, dust and organic remains all serve as a food source for fungi. Sustained high relative humidity levels, for example, of 70% and above, together with a ready food source are supportive of excess mold growth within the interior space 130 of the wall.

The device 120 will be discussed in more detail with respect to FIGS. 2-6.

Figure 2:
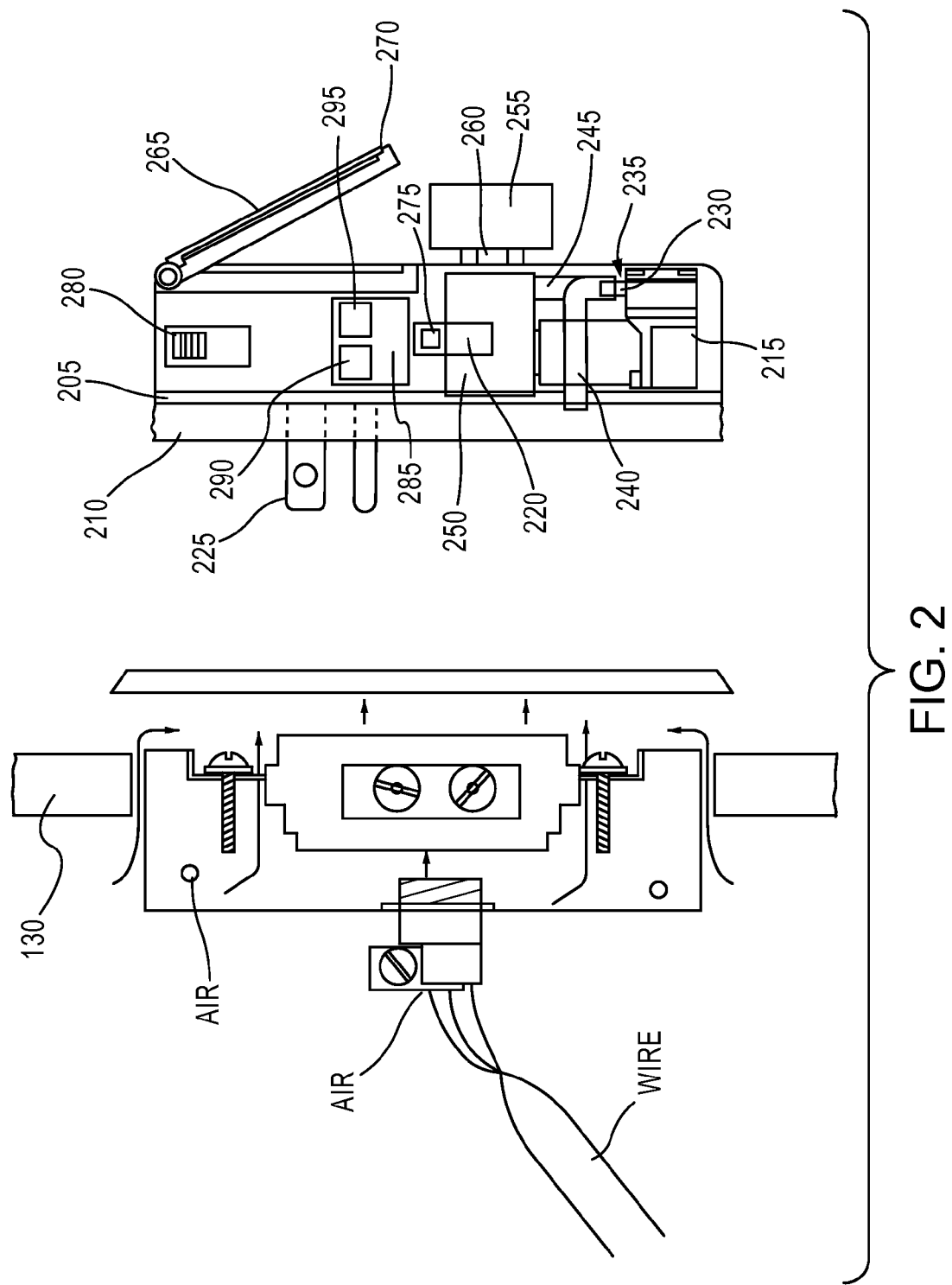
FIG. 2 shows a schematic diagram of an apparatus for monitoring and sampling air quality in an interior space of a wall, in accordance with an embodiment of the invention.

FIG. 2 shows a schematic diagram of a side view of an apparatus for monitoring and sampling air quality in an interior space of a wall, in accordance with an embodiment of the invention. The apparatus 200 includes a housing 205 which attaches the apparatus 200 to an electrical outlet in the wall, and a gasket 210 which provides a seal between the housing 205 and the electrical outlet or the wall. The apparatus 200 further includes an air moving unit 215 which draws air from the interior space of the wall into the apparatus 200, and a sensor 220 which monitors and samples the air quality in the interior space of the wall. The gasket 210 directly attaches to an electrical plate cover of the electrical outlet or to the wall.

In accordance with an embodiment of the invention, the gasket 210 provides the seal around the electrical outlet, when the gasket 210 is directly attached to the electrical plate cover. In another embodiment, the gasket 210 provides a seal around the electrical plate cover, when the gasket 210 is directly attached to the wall. The gasket 210 is made of a flexible, soft, or supple material, and effectively separates the ambient interior room air from the air in the interior space of the wall that is withdrawn through and around the electrical outlet by the apparatus 200. The seal may include a sufficient suction force to further secure the apparatus 200 to the electrical outlet or to the wall.

In accordance with an embodiment of the invention, the housing 205 includes a plug 225, for example a male plug, which attaches the apparatus 200 to the electrical outlet and/or powers the apparatus 200. In accordance with an embodiment of the invention, the plug 225 is made of a conductive material and thus configured to power the apparatus when plugged into the electrical outlet. In another embodiment, the plug 225 is made of conductive or non-conductive material and is primarily used as a mounting bracket to temporarily affix the apparatus 200 to the electrical outlet. In either embodiment, the apparatus 200 may be powered by a battery (not shown), either as a primary or secondary source of power or back-up power. The plug 225 may also include one or more enlarged prongs (i.e., with expanded dimensions or modified for additional grip within the electrical outlet). The enlarged prongs of the plug 225 enable the apparatus to be a self-supporting device (i.e., by securely holding the housing 205 of the apparatus in the electrical outlet, while at the same time securing the seal of gasket 210 between the housing 205 and the electrical outlet or the wall). In another embodiment, the enlarged prongs of the plug 225 enable the apparatus to be a self-supporting device such that the gasket 210 separates room air from interior wall air.

In accordance with an embodiment of the invention, the air moving unit 215 draws air from the interior space of the wall into the apparatus 200. The air moving unit 215 includes a fan, a pump, for example, an extraction pump, a vacuum pump, a tube pump, a sampling pump, a calibrated pump, a non-calibrated pump, or any air moving device. The size of the pump may be selected based on the need for the apparatus 200 to provide a constant flow of air. The air moving unit 215 includes a suction intake 230 and an exhaust port 235. In accordance with an embodiment of the invention, the suction intake 230 is incorporated or replaces one of the prongs of the plug 225.

In accordance with another embodiment of the invention, the apparatus 200 further includes an intake port 240 which operatively connects the air moving unit 215 (i.e., operatively connects to the suction intake 230 of the air moving unit 215) with the interior space of the wall. Using the intake port 240, the air moving unit 215 draws the air from the interior space of the wall and directs the air through an outflow connector 245, which is connected to the exhaust port 235 of the air moving unit 215, into a vented chamber 250 of the apparatus 200. The air moving unit 215 maintains a positive displacement of the air in the vented chamber 250 of the apparatus 200. In accordance with an embodiment of the invention, the vented chamber 250 includes the sensor 220 and a nipple 255. The sensor 220 measures at least one of relative humidity, absolute humidity, dew point, and temperature of the air in the interior space of the wall. Although only one sensor 220 is illustrated in FIG. 2, a plurality of sensors 220 may be included in the apparatus 200 to measure and/or monitor a plurality of air qualities.

In accordance with an embodiment of the invention, the nipple 255 connects to an exhaust port 260 of the vented chamber 250 and receives at least one of an interchangeable air sampling cartridge, a sampling media, a fungal or microbial trap, and a culture dish or cassette. The nipple 255 may also receive a cartridge containing a gas or air particulates to be introduced into the interior space of the wall.

The apparatus further includes a user display 265 configured which displays at least one of a sensor reading and an alarm. The sensor reading may include the measured psychrometric air quality values. The alarm may include a visual 270 alarm or an audible 275 alarm and may be activated when a preset condition, for example, an indication of the presence of mold, is observed. The user display 265 may pivot to assist a user of the apparatus 200 with viewing the user display 265.

In accordance with an embodiment of the invention, the apparatus 200 includes a switch 280 which controls one or more functions, for example, on/off, a timer, and a program selection for measuring various air qualities.

In accordance with an embodiment of the invention, the apparatus includes a processor 285, which includes memory 290 and computer program code 295. The computer program code 295 may be embodied on a non-transitory computer-readable medium or computer-readable storage medium. The memory 290 may be coupled to the processor 285 for storing information and instructions to be executed by the processor 285. The computer program code 295 may be encoded with instructions to control the air moving unit 215, the sensor 220, the user display 265, and the processor 285 to perform a process, such as the method shown in FIG. 5, as will be discussed in more detail below. The processor 285 controls the air moving unit 215 and the sensor 220 to monitor, measure, and record the air qualities, and the user display 265 to display the air qualities and to activate the visual alarm 270 and audio 275 alarm, for example, when specified parameters are met or exceeded, and to function as a timer to activate and deactivate run times of the air moving unit 215.

Figure 3:
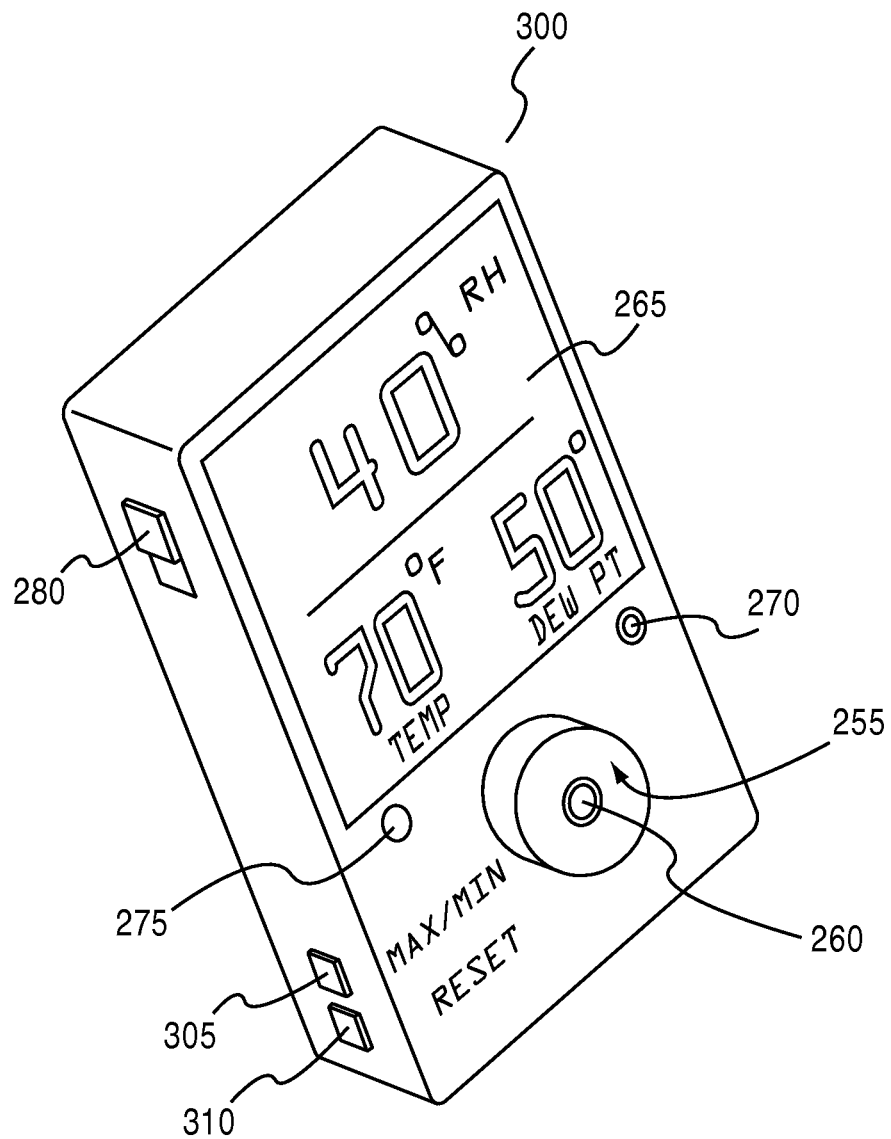
FIG. 3 shows a schematic diagram of a front exterior view of the apparatus shown in FIG. 2, in accordance with an embodiment of the invention.

FIG. 3 shows a schematic diagram of a front view of the apparatus shown in FIG. 2, in accordance with an embodiment of the invention. In addition to the nipple 255, the exhaust port 260, the user display 265, the visual alarm 270 or the audible 275 alarm, the switch 280 discussed above for the apparatus shown in FIG. 2, the apparatus 300, as shown in FIG. 3, further includes a minimum/maximum button 305 which when depressed retrieves a minimum and a maximum reading of the psychrometric air qualities, for example, the relative humidity, temperature and the temperature of the air in the interior space of the wall, from the memory 290 and displays the value(s) on the user display 265. The apparatus 300 further includes a minimum/maximum reset button 310 which when depressed resets the stored minimum and maximum readings of the psychrometric air qualities stored in the memory 290.

Figure 4:
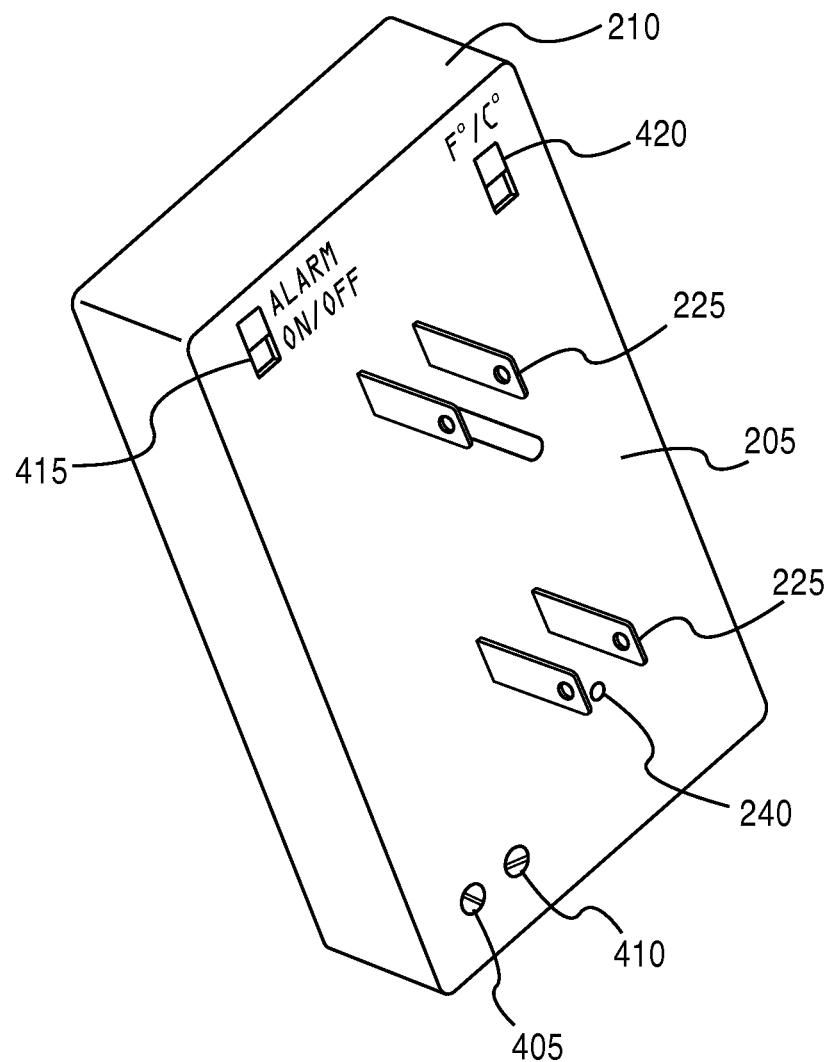
FIG. 4 shows a schematic diagram of a back exterior view of the apparatus shown in FIG. 2, in accordance with an embodiment of the invention.

FIG. 4 shows a schematic diagram of a back view of the apparatus shown in FIG. 2, in accordance with an embodiment of the invention. In addition to the housing 205, the gasket 210, the plug 225, and the intake port 240 discussed above for the apparatus shown in FIG. 2, the apparatus 400, as shown in FIG. 4, further includes a temperature sensitivity adjustment pod 405, a humidity sensitivity adjustment pod 410. The pods are used to adjust a sensitivity of a temperature or humidity sensor and to allow the electronic resistance to be calibrated to a known temperature or humidity. These pods can be field adjusted in case of variance. The apparatus 400 further includes an alarm switch 415 to turn the visual alarm 270 and audio alarm 275 on and off, and a temperature switch 420 to toggle the temperature readings between Fahrenheit and Celsius displayed readings.

Figure 5:
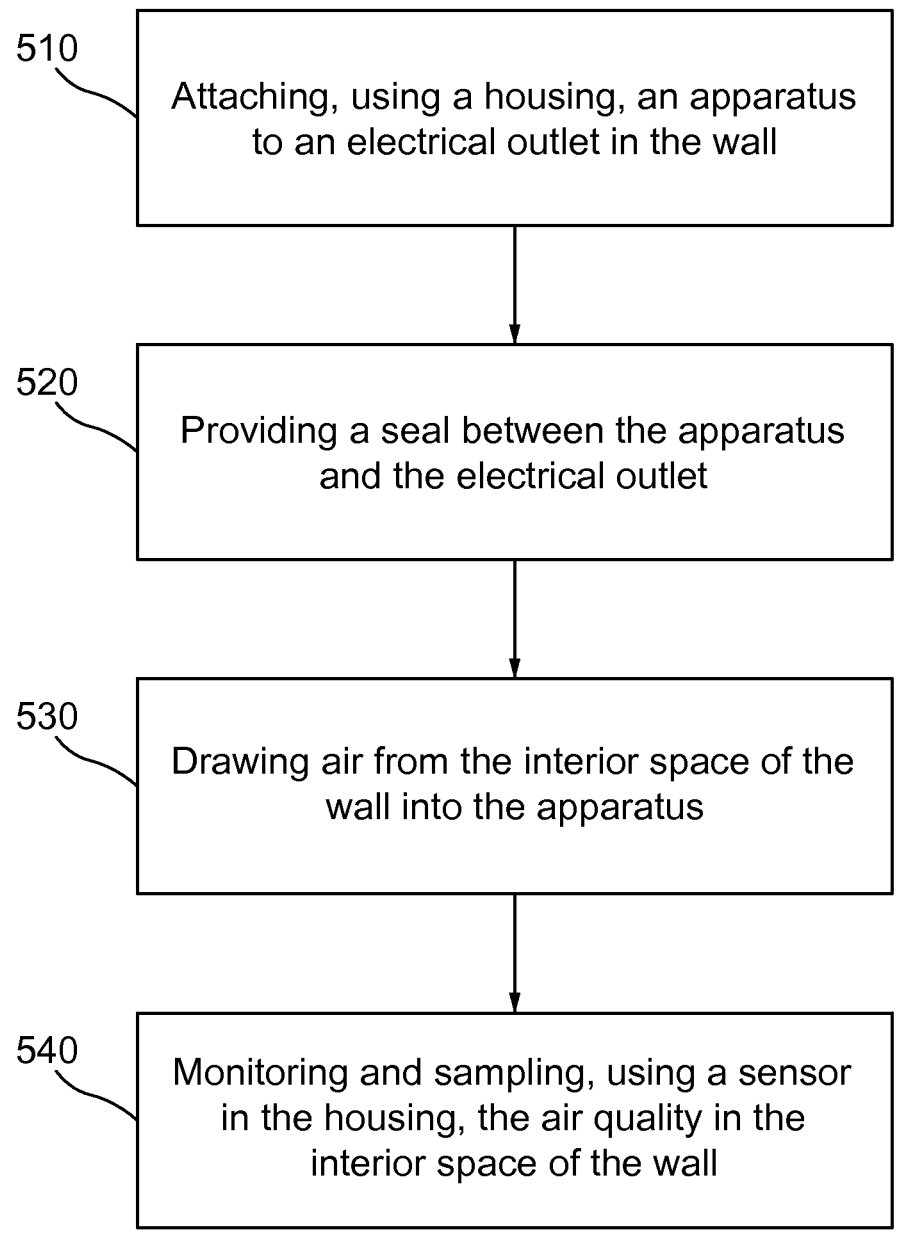
FIG. 5 shows a flow diagram of a method for monitoring and sampling air quality in an interior space of a wall, in accordance with an embodiment of the invention.

FIG. 5 shows a flow diagram of a method for monitoring and sampling air quality in an interior space of a wall, in accordance with an embodiment of the invention. The method 500 includes attaching, at step 510, using a housing, an apparatus to an electrical outlet in the wall, and providing, at step 520, a seal between the apparatus and the electrical outlet. The method further includes drawing, at step 530, air from the interior space of the wall into the apparatus, and monitoring and sampling, at step 540, using a sensor, the air quality in the interior space of the wall. The attaching includes directly attaching the apparatus to an electrical plate cover of the electrical outlet or to the wall. In accordance with another embodiment of the invention, the method further includes transferring the monitored and sampled air to least one of an interchangeable air sampling cartridge, a sampling media, a fungal or microbial trap, and a culture dish or cassette.

Figure 6:
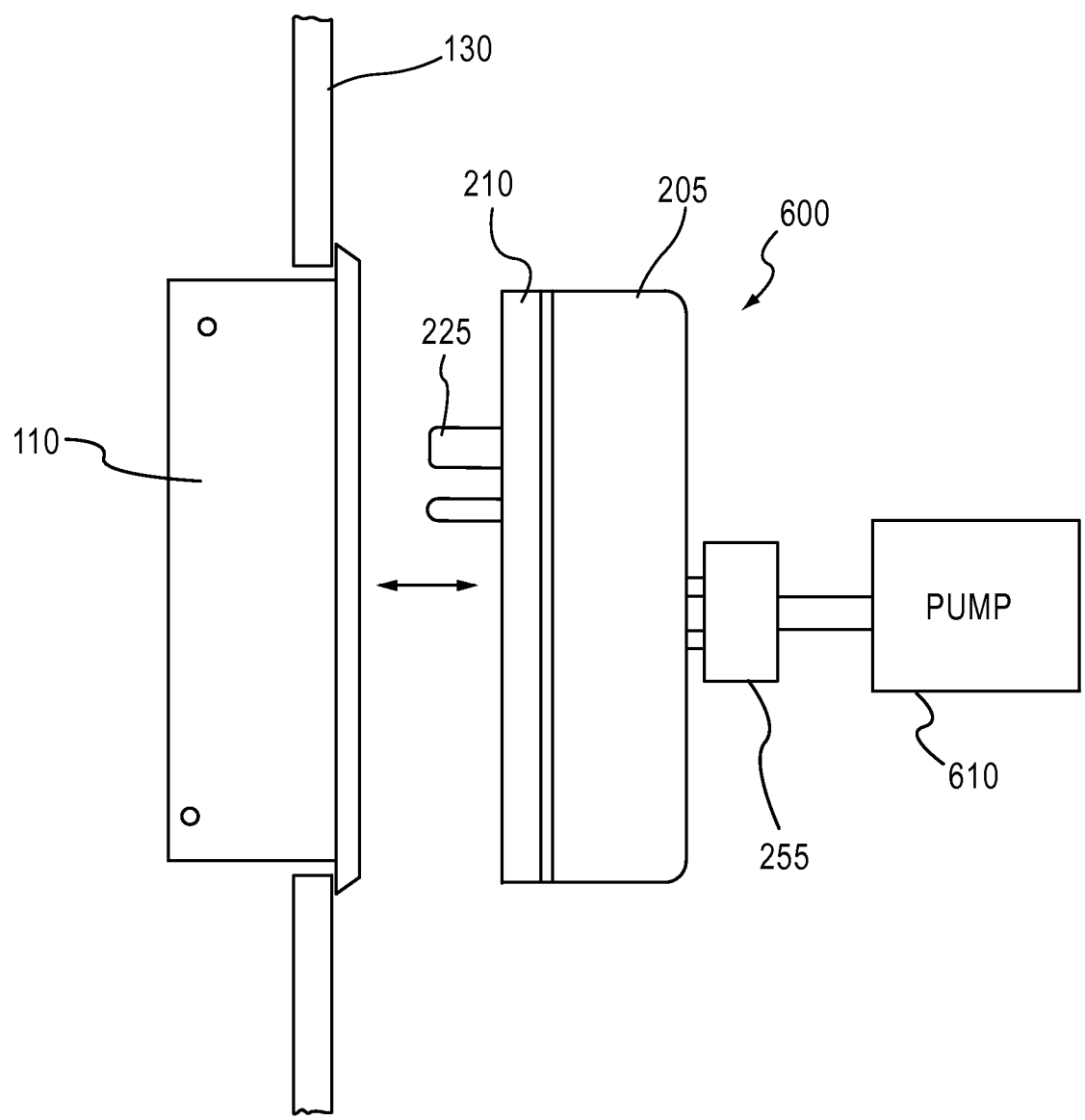
FIG. 6 shows a schematic diagram of another apparatus for monitoring and sampling air quality in an interior space of a wall, in accordance with an embodiment of the invention.

FIG. 6 shows a schematic diagram of another apparatus for monitoring and sampling air quality in an interior space of a wall, in accordance with an embodiment of the invention. The apparatus 600 is a non-mechanical embodiment which is configured to receive an external pump to displace air through the apparatus 600 into an interior space of the wall 130. The apparatus 600 includes the housing 205 configured to attach the apparatus 600 to an electrical outlet 110 in the wall 130, the gasket 210 configured to provide a seal between the housing 205 and the electrical outlet 110, the plug 225 including one or more prongs to secure the housing 205 to the electrical 110 outlet in the wall 130, and the nipple 255 operatively connected to the housing 205. The gasket 210 is configured to directly attach to an electrical plate cover of the electrical outlet 110 or to the wall 130. The nipple 255 is configured to receive a pump 610 to displace air through the apparatus 600 into an interior space of the wall 130, allowing for withdrawal of air from and for flow of air into the interior space of the wall 130. The nipple 255 may also be configured to receive a gas or air particulates to be introduced into the interior space of the wall 130.

The processor 285 may be of any type suitable to the local technical environment, and may include one or more of general purpose computers, special purpose computers, microprocessors, digital signal processors (DSPs), and processors based on multi-core processor architecture, as non-limiting examples. The computer program code 295 according to certain embodiments of the invention may be composed of modules that are in operative communication with one another, and which are designed to pass information or instructions to an electronic device.

The memory 290 may be of any type suitable to the local technical environment and may be implemented using any suitable data storage technology, machine or computer readable storage medium, such as semiconductor-based memory devices, flash memory, magnetic memory devices and systems, optical memory devices and systems, fixed memory and removable memory, as non-limiting examples.

The embodiments of the invention discussed above may be implemented by hardware, computer software executable by the processor 285, or by a combination of hardware and software.

The steps of the method, as shown in FIG. 5, described in connection with the embodiments disclosed herein can be embodied directly in hardware, in the computer program code 295 executed by the processor 285, or in a combination of the two. The computer program code 295, or product, can be embodied on a computer readable (i.e., non-transitory) storage medium. Non-transitory storage medium does not include a transitory signal. Examples of non-transitory storage medium may include, for example, a computer-readable medium, a computer distribution medium, a computer-readable storage medium, and a computer program. The computer readable storage medium may include any media or means that may contain, store, communicate, propagate or transport the instructions for use by or in connection with an instruction execution system, apparatus, or device, for example, a disk media, computer memory, or other storage device. For example, the computer program code 295 can reside in random access memory (RAM), flash memory, read-only memory (ROM), erasable programmable read-only memory (EPROM), electrically erasable programmable read-only memory (EEPROM), registers, hard disk, a removable disk, a compact disk read-only memory (CD-ROM), or any other form of storage medium known in the art. The storage medium can be coupled to the processor 285 such that the processor 285 can read information from, and write information to, the storage medium. In the alternative, the storage medium can be integral to the processor 285. The processor 285 and the storage medium can reside in an application specific integrated circuit (ASIC). In the alternative, the processor 285 and the storage medium can reside as discrete components.

Thus, in accordance with an embodiment of the invention, there is provided a computer program product embodied on a non-transitory computer readable storage medium. The computer program product is encoded with instructions to control a processor to perform a process for monitoring and sampling air quality in an interior space of a wall. The process includes attaching, using a housing, the apparatus to an electrical outlet in the wall, and providing a seal between the apparatus and the electrical outlet. The process further includes drawing air from the interior space of the wall into the apparatus, and monitoring and sampling, using a sensor, the air quality in the interior space of the wall. The attaching includes directly attaching the apparatus to an electrical plate cover of the electrical outlet or to the wall.

One having ordinary skill in the art will readily understand that the invention as discussed above may be practiced with steps in a different order than those which are disclosed. Therefore, although the invention has been described based upon these preferred and non-limiting embodiments, it would be apparent to those of skill in the relevant art that certain modifications, variations, and alternative constructions would be apparent, while remaining in the spirit and scope of the invention. Thus, the embodiments do not limit the invention to the particular listed devices and technologies. In order to determine the metes and bounds of the invention, therefore, reference should be made to the appended claims.

I claim:

1. An apparatus for monitoring and sampling air quality in an interior space of a wall, the apparatus comprising:
    a housing configured to attach the apparatus to an electrical outlet in the wall;
    a gasket configured to provide a seal between the housing and the electrical outlet;
    an air moving unit configured to draw air from the interior space of the wall into the apparatus; and
    a sensor configured to monitor and sample the air quality in the interior space of the wall,
    wherein the gasket is configured to directly attach to an electrical plate cover of the electrical outlet or to the wall.

2. The apparatus of claim 1, wherein the seal comprises a sufficient suction force to secure the apparatus to the electrical outlet or to the wall.

3. The apparatus of claim 1, wherein the gasket is further configured to provide the seal around the electrical outlet, when the gasket is directly attached to the electrical plate cover, and wherein the gasket is further configured to provide the seal around the electrical plate cover, when the gasket (4) is directly attached to the wall.

4. The apparatus of claim 1, wherein the housing comprises a plug, wherein the plug is configured to at least one of attach the apparatus to the electrical outlet and to power the apparatus.

5. The apparatus of claim 4, wherein the plug comprises one or more enlarged prongs.

6. The apparatus of claim 1, wherein the air moving unit comprises a fan or a pump.

7. The apparatus of claim 1, further comprising:
    an intake port configured to operatively connect the air moving unit with the interior space of the wall; and
    a vented chamber,
    wherein the air moving unit is further configured to draw the air from the interior space of the wall using the intake port and direct the air into the vented chamber of the apparatus.

8. The apparatus of claim 7, wherein the air moving unit is further configured to maintain a positive displacement of the air in the vented chamber of the apparatus.

9. The apparatus of claim 7, wherein the vented chamber comprises the sensor.

10. The apparatus of claim 1, wherein the sensor is configured to measure at least one of relative humidity, absolute humidity, dew point, and temperature.

11. The apparatus of claim 7, further comprising:
    a nipple operatively connected to the vented chamber.

12. The apparatus of claim 11, wherein the nipple is configured to receive at least one of an interchangeable air sampling cartridge, a sampling media, a fungal or microbial trap, and a culture dish or cassette.

13. The apparatus of claim 1, further comprising:
    a user display configured to display at least one of a sensor reading, a visual alarm, and an audible alarm.

14. The apparatus of claim 1, further comprising:
    a battery configured to provide power to the apparatus.

15. The apparatus of claim 1, further comprising:
    a processor; and
    memory including computer program code,
    wherein the memory and the computer program code are configured to, with the processor, cause the apparatus at least to
    control the air moving unit to draw the air from the interior space of the wall into the apparatus, and
    control the sensor to monitor and sample the air quality in the interior space of the wall.

16. An apparatus for monitoring and sampling air quality in an interior space of a wall, the apparatus comprising:
    a housing configured to attach the apparatus to an electrical outlet in the wall;
    a gasket configured to provide a seal between the housing and the electrical outlet;
    a plug comprising one or more prongs to secure the housing to the electrical outlet in the wall; and
    a nipple operatively connected to the housing,
    wherein the gasket is configured to directly attach to an electrical plate cover of the electrical outlet or to the wall, and
    wherein the nipple is configured to receive a pump to displace air through the apparatus into an interior space of the wall.

17. The apparatus of claim 16, wherein the nipple is configured to receive a gas or air particulates to be introduced into the interior space of the wall.

18. An apparatus for monitoring and sampling air quality in an interior space of a wall, the apparatus comprising:
    attaching means for attaching the apparatus to an electrical outlet in the wall;
    sealing means for providing a seal between the attaching means and the electrical outlet;
    air moving means for drawing air from the interior space of the wall into the apparatus; and sensing means for monitoring and sampling the air quality in the interior space of the walls, wherein the sealing means is for directly attaching the apparatus to an electrical plate cover of the electrical outlet or to the wall.

19. A method for monitoring and sampling air quality in an interior space of a wall, the method comprising attaching, using a housing, the apparatus to an electrical outlet in the wall;

providing a seal between the apparatus and the electrical outlet;

drawing air from the interior space of the wall into the apparatus; and monitoring and sampling, using a sensor, the air quality in the interior space of the wall, wherein the attaching comprises directly attaching the apparatus to an electrical plate cover of the electrical outlet or to the wall.

20. The method of claim 19, further comprising:

transferring the monitored and sampled air to least one of an interchangeable air sampling cartridge, a sampling media, a fungal or microbial trap, and a culture dish or cassette.

21. A computer program product embodied on a non-transitory computer readable storage medium, the computer program product being encoded with instructions to control a processor to perform a process for monitoring and sampling air quality in an interior space of a wall, the process comprising:

attaching, using a housing, an apparatus to an electrical outlet in the wall;

providing a seal between the apparatus and the electrical outlet;

drawing air from the interior space of the wall into the apparatus; and monitoring and sampling, using a sensor, the air quality in the interior space of the wall, wherein the attaching comprises directly attaching the apparatus to an electrical plate cover of the electrical outlet or to the wall.

* * * * *